United States Patent
Hunter et al.

(10) Patent No.: US 9,205,176 B2
(45) Date of Patent: Dec. 8, 2015

(54) ANISOTROPIC POROUS SCAFFOLDS

(71) Applicant: Zimmer, Inc., Warsaw, IN (US)

(72) Inventors: Christopher J. Hunter, Warsaw, IN (US); Oludele O. Popoola, Granger, IN (US)

(73) Assignee: Zimmer, Inc., Warsaw, IN (US)

(*) Notice: Subject to any disclaimer, the term of this patent is extended or adjusted under 35 U.S.C. 154(b) by 197 days.

(21) Appl. No.: 13/903,322

(22) Filed: May 28, 2013

(65) Prior Publication Data
US 2013/0325142 A1    Dec. 5, 2013

Related U.S. Application Data

(60) Provisional application No. 61/653,510, filed on May 31, 2012.

(51) Int. Cl.
| | |
|---|---|
| C22F 1/18 | (2006.01) |
| B21D 37/16 | (2006.01) |
| A61F 2/28 | (2006.01) |
| A61L 27/56 | (2006.01) |
| C22C 1/08 | (2006.01) |
| A61F 2/44 | (2006.01) |
| A61L 27/04 | (2006.01) |
| A61L 27/50 | (2006.01) |
| A61F 2/30 | (2006.01) |
| A61C 8/00 | (2006.01) |

(52) U.S. Cl.
CPC . *A61L 27/56* (2013.01); *A61F 2/28* (2013.01); *A61F 2/4455* (2013.01); *A61L 27/04* (2013.01); *A61L 27/50* (2013.01); *C22C 1/08* (2013.01); *A61C 2008/0046* (2013.01); *A61F 2/3094* (2013.01); *A61F 2002/30011* (2013.01); *A61F 2002/30065* (2013.01); *A61F 2002/3092* (2013.01); *A61F 2310/00011* (2013.01); *A61F 2310/00395* (2013.01); *A61L 2430/02* (2013.01); *A61L 2430/38* (2013.01); *B22F 2998/10* (2013.01)

(58) Field of Classification Search
CPC .............. C22F 1/18; C22F 1/10; A61L 27/56
See application file for complete search history.

(56) References Cited

U.S. PATENT DOCUMENTS

| | | | |
|---|---|---|---|
| 5,282,861 | A | 2/1994 | Kaplan |
| 5,454,815 | A | 10/1995 | Geisser et al. |

(Continued)

FOREIGN PATENT DOCUMENTS

| | | |
|---|---|---|
| DE | 102008050804 A1 | 4/2010 |
| EP | 2855722 A1 | 4/2015 |

(Continued)

OTHER PUBLICATIONS

"International Application Serial No. PCT/US2013/042856, International Preliminary Report on Patentability mailed Dec. 11, 2014", 7 pgs.

(Continued)

*Primary Examiner* — Jessee Roe
(74) *Attorney, Agent, or Firm* — Schwegman Lundberg & Woessner, P.A.

(57) ABSTRACT

A method of fabricating an anisotropic porous scaffold includes heating a previously-formed porous metal scaffold to permit deformation of a material of the previously-formed porous metal scaffold, and deforming, while heated, the previously-formed porous metal scaffold in at least a first direction.

21 Claims, 8 Drawing Sheets

(56) References Cited

U.S. PATENT DOCUMENTS

| | | |
|---|---|---|
| 5,681,315 A | 10/1997 | Szabo |
| 6,660,041 B1 | 12/2003 | Grundei |
| 7,799,075 B2 * | 9/2010 | Kang et al. ............ 623/10 |
| 7,955,337 B2 | 6/2011 | Lee |
| 2005/0100578 A1 * | 5/2005 | Schmid et al. ............ 424/423 |
| 2007/0104941 A1 | 5/2007 | Kameda et al. |
| 2009/0075382 A1 | 3/2009 | Sachlos |
| 2009/0098183 A1 | 4/2009 | Detamore et al. |
| 2010/0137990 A1 | 6/2010 | Apatsidis et al. |

FOREIGN PATENT DOCUMENTS

| | | |
|---|---|---|
| WO | WO-2009108299 A1 | 9/2009 |
| WO | WO-2012006188 A1 | 1/2012 |
| WO | WO-2012065729 A1 | 5/2012 |
| WO | WO-2013181141 A1 | 12/2013 |
| WO | WO-2013181141 A8 | 12/2013 |

OTHER PUBLICATIONS

"International Application Serial No. PCT/US2013/042856, International Search Report mailed Nov. 6, 2013", 4 pgs.

"International Application Serial No. PCT/US2013/042856, Written Opinion mailed Nov. 6, 2013", 5 pgs.

Ryan, Garrett E, et al., "Porus titanium scaffolds fabricated using a rapid prototyping and powder metallurgy technique", Biomaterials, Elsevier Science Publishers, vol. 29, No. 27, (Sep. 1, 2008), 3625-3635.

* cited by examiner

Fig. 9

ANISOTROPIC POROUS SCAFFOLDS

CLAIM OF PRIORITY

This application claims the benefit of U.S. Provisional Patent Application Ser. No. 61/653,510, filed on May 31, 2012, the benefit of priority of which is claimed hereby, and is incorporated by reference herein in its entirety.

BACKGROUND

Prosthetic devices can replace or augment body components or portions of body components that cannot be regenerated or are no longer functioning properly. Examples of prosthetic devices include heart valves, pacemakers, spinal implants, dental implants, breast implants, collagen for soft tissue augmentation, and orthopedic devices, such as artificial knee, hip, and ankle joints.

Some prosthetic implants can include a porous scaffold material, such as to provide structural support to an orthopedic implant, to fill a void in bone reconstruction or joint repair, or to provide a structure for permitting ingrowth and attachment of tissue. Porous scaffolds can be used to provide structural support to a patient's tissue, such as bone tissue. Porous scaffolds can also be used to provide an attachment structure for a patient's tissue to couple or attach, such as via ingrowth and bonding between the patient's tissue and the porous scaffold.

SUMMARY

This disclosure describes methods of making an anisotropic porous scaffold for prosthetic implants, such as orthopedic implants for bone reconstruction or joint repair. Anisotropic porous scaffolds can mimic tissue properties, which are generally also anisotropic. The present methods can permit control of a direction of anisotropy of the scaffold. This can permit a stiffness or strength of the scaffold to be adjusted or altered in a desired direction.

In an example, a method of fabricating an anisotropic porous scaffold comprises heating a previously-formed porous metal scaffold to permit deformation of a material of the previously-formed porous metal scaffold, and deforming, when heated, the previously-formed porous metal scaffold in at least a first direction.

In an example, a porous scaffold comprises a plurality of cells defined by ligaments where the plurality of cells are interconnected by pores and where the ligaments provide for a physical property of the porous scaffold, with a value of the physical property in a first direction being different from a value of the physical property in a second direction that is different than the first direction.

This summary is intended to provide an overview of subject matter of the present disclosure. It is not intended to provide an exclusive or exhaustive explanation of the invention. The detailed description is included to provide further information about the present disclosure.

BRIEF DESCRIPTION OF THE DRAWINGS

In the drawings, like numerals can be used to describe similar elements throughout the several views. Like numerals having different letter suffixes can be used to represent different views of similar elements. The drawings illustrate generally, by way of example, but not by way of limitation, various embodiments discussed in the present document.

DETAILED DESCRIPTION

This disclosure describes methods of making an anisotropic porous scaffold. The anisotropic porous scaffold can be used in prosthetic implants, such as orthopedic implants for bone reconstruction or joint repair. The method can include deforming a previously-formed porous scaffold, such as an isotropic porous scaffold, to achieve a desired anisotropy.

The previously-formed porous scaffold can be deformed selectively, such as to achieve a physical property of the porous scaffold that is the same or substantially the same as a corresponding physical property of a patient's tissue. Deformation can be accomplished by heating a previously-formed porous scaffold to permit deformation of the material of the previously-formed porous scaffold. Then, the heated porous scaffold can be deformed in at least a first direction, such as by compressing or stretching.

An example of a porous scaffold for prosthetic implants, such as orthopedic bone restoration or joint repair implants, described in U.S. Pat. No. 5,282,861 to Kaplan, entitled "Open Cell Tantalum Structures For Cancellous Bone Implants and Cell and Tissue Receptors," which is incorporated herein by reference. A porous scaffold, TRABECULAR METAL™, is available from Zimmer, Inc., such as for orthopedic implants.

Previous porous scaffold materials are generally structurally isotropic. The term "isotropic" or "structurally isotropic," when referring to a porous scaffold, generally refers to the physical properties of the scaffold being equal or substantially equal, or uniform or substantially uniform in all directions. In an example, a porous scaffold can be considered to have physical properties that are "substantially equal" or "substantially uniform," such that the porous scaffold is a structurally isotropic scaffold, if a value of the physical properties in a first direction are within about 5% of the value of the physical structure in all or substantially all other directions of the porous scaffold, such as within 3%, within 2%, within 1%, within 0.5%, or within 0.1%.

Figure 1A:
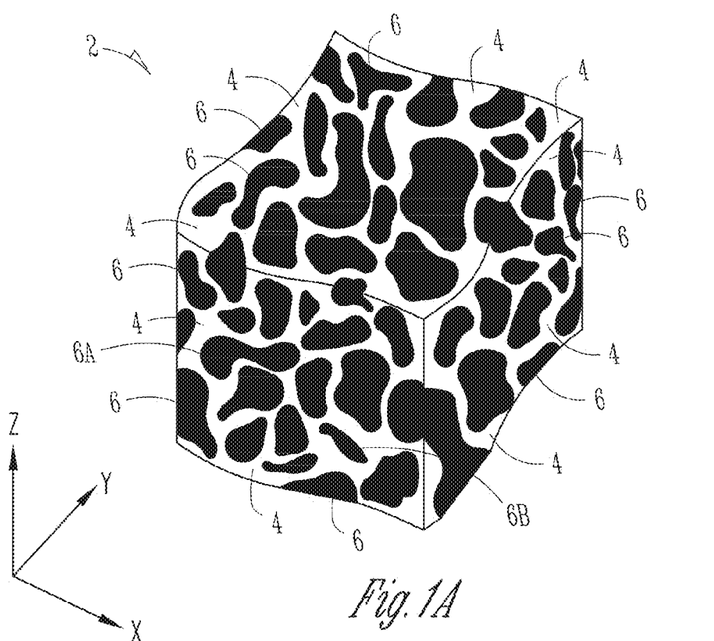
FIG. 1A is a perspective view of an example of an isotropic porous scaffold.

FIG. 1A shows an example of an isotropic porous scaffold 2, such as can be used to provide support to a patient's bone. The isotropic porous scaffold 2 can include a plurality of ligaments 4. The ligaments 4 can define a plurality of open cells 6, wherein a plurality of the cells 6 are interconnected by pores. The overall porosity of this example of the isotropic porous scaffold 2 can be within a range from about 20% to about 90%, such as within a range from about 50% to about 80%. In various examples, the porous scaffold 2 can have a porosity of at least about 60%, 70%, 80%, or 90%. Depending on the particular materials and application, an acceptable range of porosity can be within a range from 20% to 80%. Most of the cells 6 can be interconnected. This can help allow or promote ingrowth of tissue or bone growth promoting cells, or both, into and throughout the cells 6. In various examples, at least about 60%, 70%, 80%, 90%, 95%, 99%, or even 100% of the cells 6 can be interconnected.

As described above, the isotropic porous scaffold 2 can have substantially the same physical properties in any direction. Such isotropy can be evaluated along arbitrarily selected mutually orthogonal X, Y, and Z directions, such as shown in FIG. 1A, or any other direction. Examples of physical properties that can be isotropic can include stiffness, failure strength, compressive strength, tensile strength, or elastic modulus.

The physical properties of the porous scaffold 2 can be affected by the orientation of the ligaments 4 and the cells 6. A porous scaffold 2 can be structurally isotropic overall even if individual cells 6 or groups of cells 6, on the microscopic scale, are anisotropic. For example, some cells 6, such as cells 6A and 6B, can be individually anisotropic, such as having a length in a particular direction (e.g., the X direction) that is longer than a width in another direction (e.g., the Z direction). However, as a whole, the porous scaffold 2 can still be isotropic overall.

Human or animal tissue is generally not structurally isotropic. For example, cancellous bone includes trabeculae, also referred to as spicules, defining a plurality of open spaces. The trabeculae and open spaces are generally oriented in a direction of principle stress (e.g., axially along a long bone such as a femur). The trabeculae form a porous or spongy-type tissue that is generally stiffer in a particular direction. For example, cancellous bone in the femur is generally stiffer axially than radially to accommodate an axial direction of the primary stress on the bone.

A prosthetic porous scaffold used as a substitute for cancellous bone should avoid producing load concentrations within the structural support, which can lead to stress shielding of nearby bone. Bone can remodel to adapt to the load applied to it. If a particular location within a bone experiences increased load, the body will increase bone growth at that location. The reverse is also true. In response to a reduced load at a particular location, the body will tend to resorb bone from that location. Therefore, concentrating stresses within a prosthetic implant providing structural support can lead to weakening and resorption of the surrounding bone.

The isotropy of porous scaffold 2, together with the anisotropy of nearby bone, can lead to stress shielding, such as if the isotropic porous scaffold 2 is stiffer in one direction (e.g., in a radial direction, for a long bone such as a femur) than the nearby native bone. An anisotropic porous scaffold support structure can help reduce or avoid such stress shielding, such as by providing anisotropy in a similar direction to the anisotropy of the nearby native bone.

For example, for bone, the porous scaffold can be configured so that an anisotropy of a physical property, such as stiffness, compressive strength, elastic modulus, and the like, is the same or substantially the same as an anisotropy of the same physical property in the native bone. In an example, the porous scaffold can be configured to be stiffer in a first direction (e.g., axially) compared to a second direction (e.g., laterally), such as to mimic anisotropic stiffness of nearby native bone in the first direction and second direction. The porous scaffold can be configured so that the physical property, such as stiffness, is the same or substantially the same as the same physical property in the nearby native bone in both the first direction and the second direction. In an example, "substantially the same," when referring to the matching of a physical property between the porous scaffold and the nearby native bone can refer to the value of the physical property of the porous scaffold in the first direction being within 5% of the value of the physical property of the nearby native bone in the first direction, such as within 4%, 3%, 2%, 1%, 0.5%, or 0.1%. Similarly, the physical property in the second direction can be considered to be substantially the same if the value of the physical property of the porous scaffold in the second direction is within 5%, or within 4%, 3%, 2%, 1%, 0.5%, or 0.1%, of the value of the physical property of the nearby native bone in the second direction.

Figure 1B:
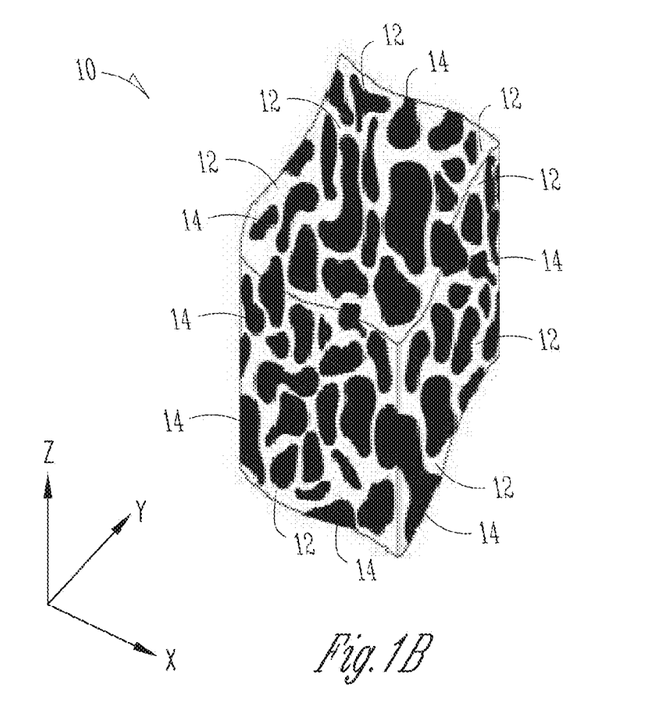
FIG. 1B is a perspective view of an example of an anisotropic porous scaffold formed by deforming the isotropic porous scaffold of FIG. 1A.

FIG. 1B shows an example of an anisotropic porous scaffold 10. The anisotropic porous scaffold 10 can include ligaments 12 that define a plurality of cells 14, wherein a plurality of the cells 14 are interconnected by pores. The term "anisotropic" or "structurally anisotropic," when referring to a porous scaffold, generally refers to a scaffold that is not "isotropic" or "structurally isotropic," as described above.

For example, the anisotropic porous scaffold 10 that can be used to provide support to a patient's bone can be stiffer in a first direction, e.g., a Z-direction as shown in FIG. 1B, than in other directions, e.g., the X and Y directions shown in FIG. 1B. This is because the ligaments 12 can be more densely packed in the Z-direction, resulting in a greater stiffness in that direction. The anisotropic porous scaffold 10 can be configured to provide one or more other anisotropic physical properties, such as stiffness, failure strength, compressive strength, tensile strength, or elastic modulus.

An isotropic porous scaffold can be deformed to form the anisotropic porous scaffold. For example, the anisotropic porous scaffold 10 can be made by deforming the previously-formed isotropic porous scaffold 2. The isotropic porous scaffold 2 can first be made, such as by chemical vapor deposition (CVD) of a metal onto a carbon substrate having substantially the same general shape as the resulting porous scaffold 2, such as described in U.S. Pat. No. 5,282,861 to Kaplan. This can include CVD of a metal, such as tantalum, niobium, titanium, or alloys thereof, onto a carbon foam substrate, resulting in a porous metal foam-like structure, such as a porous tantalum foam, a porous niobium foam, or a porous titanium foam.

Making isotropic porous scaffold 2 can include first forming a polymeric foam, such as polyurethane, with a desired pore structure. The polymeric foam can be engineered to provide one or more of a desired pore size or range of pore sizes, a desired pore shape or pore shapes, a desired aspect ratio or aspect ratios of the pores, or a desired interconnectivity or range of interconnectivities.

Next, the polymeric foam can be converted to a support scaffold. This can include chemically treating and pyrolyzing the polymeric foam to form a carbon scaffold. The polymeric foam can be pyrolyzed such that the resulting elemental carbon scaffold has substantially the same geometry as the original polymeric foam (e.g., with pores in substantially the same location with substantially the same pore size, substantially the same pore shape, substantially the same aspect ratio, and substantially the same interconnectivity). In an example, the pyrolyzed polymeric foam can form a reticulated vitreous carbon.

After being formed, the support scaffold can be shaped into a desired shape. This can include machining, cutting, or otherwise shaping the support scaffold, such as to provide the desired final macroscopice shape of the porous support scaffold.

After shaping the support scaffold, a metal can be deposited or otherwise incorporated into the support scaffold, such as via thermal or other CVD. For example, a shaped reticulated vitreous carbon or other support scaffold can be placed in a reactor in which pure tantalum can be vaporized at high temperature, such as within a chlorination chamber to form tantalum petrachloride gas ($TaCl_5$). The tantalum petrachloride gas can be reacted, such as with hydrogen gas, which can allow tantalum metal to be deposited on the support scaffold while gaseous hydrogen chloride (HCl) exits the CVD chamber.

The CVD of the tantalum or other metal can form a substantially uniform thin film of the tantalum or other metal onto the support scaffold, while leaving substantially the same open cell structure as the support scaffold. The metal deposition can form a nanotextured structure on the surface of the support scaffold. The nanotextured surface can help promote attachment of bone tissue or soft tissue to the scaffold. Materials other than tantalum can be additionally or alternatively deposited onto the support scaffold, such as, but not limited to, niobium, hafnium, tungsten, titanium, an alloy comprising at least one of tantalum, niobium, hafnium, tungsten, or titanium, or a biocompatible polymeric material, such as polyether ether ketone (PEEK) or high-density polyethylene.

After depositing the metal or other material onto the support scaffold, the surface of the deposited material can be further shaped, such as by machining This can include electric discharge machining, in which an electric arc can be used to machine the surface of the metal, such as to help ensure that the nanotextured surface or pores are not compromised or occluded.

In other embodiments, a previously-formed open porous metal structure may comprise an open cell polyurethane foam substrate coated with Ti-6Al-4V alloy using a low temperature arc vapor deposition process. Ti-6Al-4V beads may then be sintered to the surface of the Ti-6Al-4V-coated polyurethane foam substrate. Additionally, another embodiment of an open porous metal structure may comprise a metal substrate combined with a Ti-6Al-4V powder and a ceramic material, which is sintered under heat and pressure. The ceramic particles may thereafter be removed leaving voids, or pores, in the substrate. An open porous metal structure may also comprise a Ti-6Al-4V powder which has been suspended in a liquid and infiltrated and coated on the surface of a polyurethane substrate. The Ti-6Al-4V coating may then be sintered to form a porous metal structure mimicking the polyurethane foam substrate. Further, another embodiment of an open porous metal structure may comprise a porous metal substrate having particles, comprising altered geometries, which are sintered to a plurality of outer layers of the metal substrate. Additionally, an open porous metal structure may be fabricated according to electron beam melting (EBM) and/or laser engineered net shaping (LENS). For example, with EBM, metallic layers (comprising one or more of the biomaterials, alloys, and substrates disclosed herein) may be coated (layer by layer) on an open cell substrate using an electron beam in a vacuum. Similarly, with LENS, metallic powder (such as a titanium powder, for example) may be deposited and coated on an open cell substrate by creating a molten pool (from a metallic powder) using a focused, high-powered laser beam.

An anisotropic porous scaffold, such as the anisotropic porous scaffold 10, can be formed by selectively deforming the isotropic porous scaffold 2. This can include first heating the porous scaffold 2 to permit deformation of the material of the porous scaffold 2. Then, the heated porous scaffold 2 can be deformed in at least a first direction to obtain a desired shape of the anisotropic porous scaffold 10.

The temperature that is sufficient to permit deformation can be a temperature that is sufficient to permit increased deformation of the porous scaffold 2, which can be referred to herein as a "deformation temperature." A deformation temperature in a metal, such as tantalum, can be a temperature that is below a solid-state transition temperature (e.g., the melting temperature) at which the crystal or other microstructure of the material is significantly modified. For many metals, a deformation temperature can occur at between about 40% and about 80%, inclusive of the material's absolute melting temperature (e.g., the melting temperature expressed on a thermodynamic temperature scale, such as Kelvin), such as between about 50% and about 70%, inclusive, of the absolute melting temperature, for example between about 55% and about 65%, inclusive, of the absolute melting temperature, such as about 60% of the absolute melting temperature. For tantalum, for example, the melting temperature is about 3290° K (about 3017° C.), so a deformation temperature can occur between about 1315° K (about 1042° C.) and about 2635° K (about 2362° C.), inclusive, for example between about 1645° K (about 1372° C.) and about 2305° K (about 2032° C.), inclusive, such as between about 1805° K (about 1532° C.) and about 2140° K (about 1867° C.), inclusive, for example about 1975° K (about 1700° C.). It can be desirable to heat the porous scaffold beyond the deformation temperature, such as by about 10° C. to about 100° C., or by about 25° C. to about 50° C., or by about 0.5% to about 5%, or by about 1% to about 3% of the deformation temperature on an absolute temperature scale, such as Kelvin. The heated porous scaffold 2 can be deformed by actively or passively (e.g., via gravity) compressing or stretching (e.g., exerting a tensile force on) at least a portion of the heated porous scaffold 2.

Figure 2A:
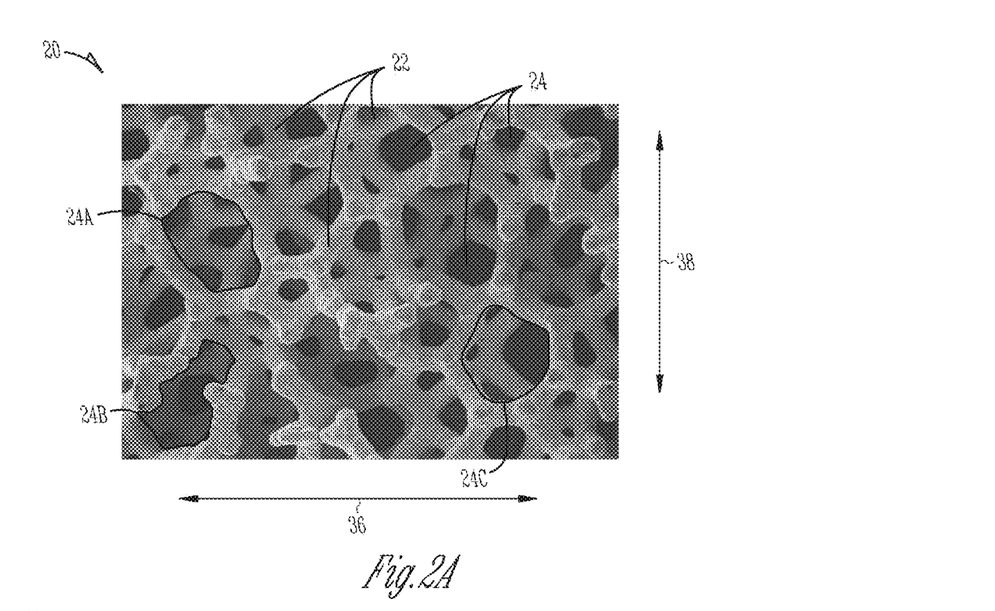
FIG. 2A is an electron micrograph of an example of an isotropic porous scaffold.
Figure 2B:
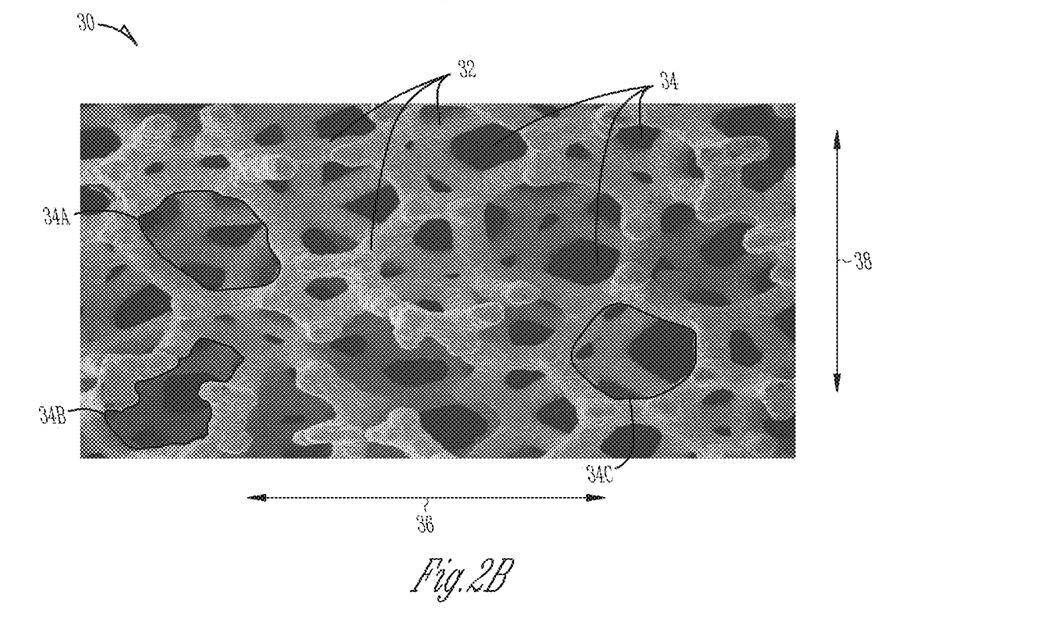
FIG. 2B is an electron micrograph of an example of an anisotropic porous scaffold formed by deforming the isotropic porous scaffold of FIG. 2A

FIGS. 2A and 2B show an electron micrograph (SEM) of an example of a porous scaffold before deforming (FIG. 2A) and after deforming (FIG. 2B). FIG. 2A is a SEM of a orthopedic implant including an isotropic porous scaffold 20 available under the trade name TRABECULAR METAL™ by Zimmer, Inc., Warsaw, Ind., USA. Like the isotropic porous scaffold 2, the isotropic porous scaffold 20 includes ligaments 22 defining cells 24. The isotropic scaffold 20 has an open-pore structure, in which a substantial portion of the cells 24 are interconnected by pores. In various examples, at least about 80%, 90%, 95%, 99%, or even 100% of the pores can be interconnected by pores.

FIG. 2B is an SEM of an anisotropic porous scaffold 30 formed by deforming the isotropic porous scaffold 20. The ligaments 32 of the anisotropic porous scaffold 30 are the deformed ligaments 22 of isotropic porous scaffold 20. The ligaments 32 define cells 34 interconnected by pores. The anisotropic porous scaffold 30 can be formed by heating the isotropic porous scaffold 20 to or beyond a deformation temperature, then deforming the isotropic porous scaffold 20 to change the isotropy of the cells 24 in at least one direction. In the example of FIGS. 2A and 2B, the isotropic porous scaffold 20 was stretched laterally outwardly in a horizontal direction 36. As a result, at least some of the ligaments 32 and at least some of the cells 34 are stretched in the horizontal direction 36. For example, a first cell 24A, a second cell 24B, and a third cell 24C of the isotropic porous scaffold 20 (FIG. 2A) have been stretched in the horizontal direction 36 to form a corresponding first cell 34A, a corresponding second cell 34B, and a corresponding third cell 34C, respectively, of the anisotropic porous scaffold 30 (FIG. 2B). As shown in FIGS. 2A and 2B, the first cell 34A has a greater width in the horizontal direction 36 than first cell 24A, while having a height in a vertical direction 38 that is substantially similar to a height of the first cell 24A in the vertical direction 38. Similarly, the second cell 34B has a greater width in the horizontal direction 36 than second cell 24B and the third cell 34C has a greater width in the horizontal directions 36 than the third cell 24C, while each has a height in the vertical direction 38 that is substantially similar to the heights of the second cell 24B and the third cell 24C.

Figure 3A:
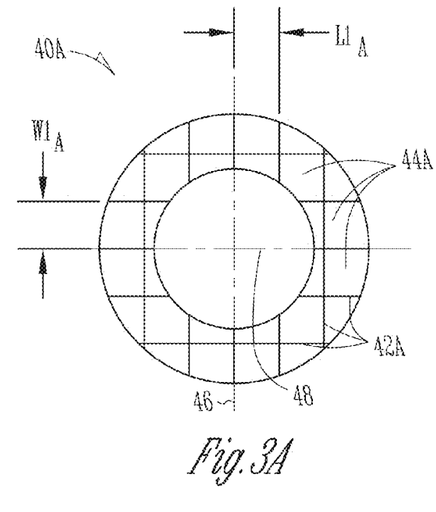
FIG. 3A is a schematic diagram of an example of an isotropic porous scaffold.
Figure 3B:
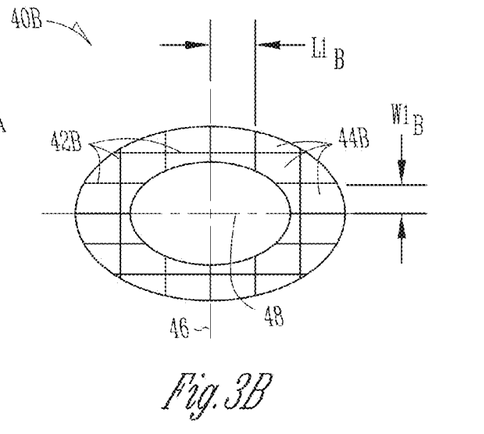
FIG. 3B is a schematic diagram of an example of an anisotropic porous scaffold formed by deforming the isotropic porous scaffold of FIG. 3A.
Figure 4A:
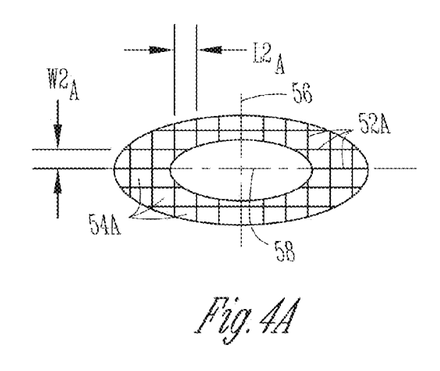
FIG. 4A is a schematic diagram of an example of an isotropic porous scaffold.
Figure 4B:
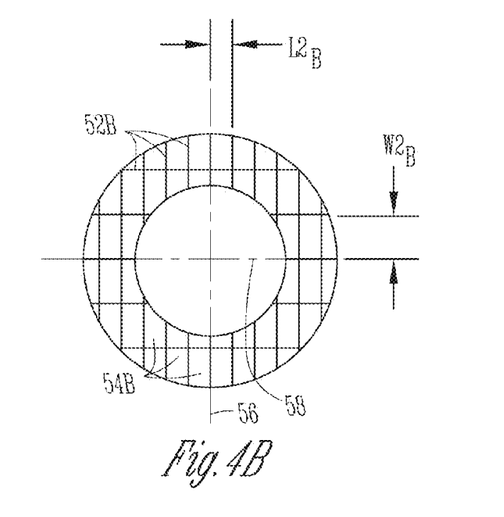
FIG. 4B is a schematic diagram of an example of an anisotropic porous scaffold formed by deforming the isotropic porous scaffold of FIG. 4A.
Figure 5A:
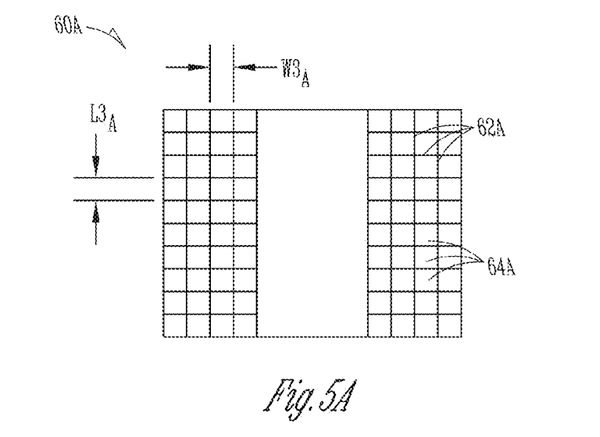
FIG. 5A is a schematic cross-sectional view of an example of an isotropic porous scaffold.
Figure 5B:
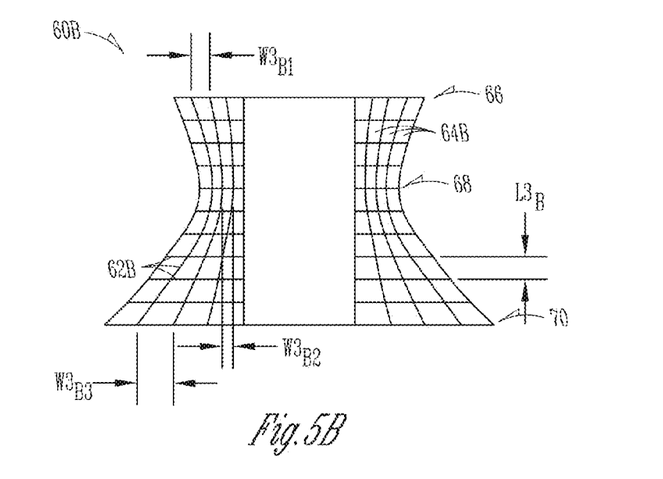
FIG. 5B is a schematic cross-sectional view of an example of an anisotropic porous scaffold formed by deforming the isotropic porous scaffold of FIG. 5A.
Figure 5C:
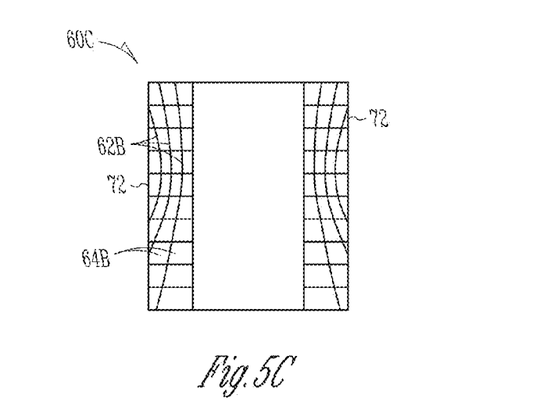
FIG. 5C is a schematic cross-sectional view of an example of an anisotropic porous scaffold formed by shaping the anisotropic porous scaffold of FIG. 5B

FIGS. 3-5 schematically show different examples of customizing an anisotropic porous scaffold to have different structural properties in different directions.

FIG. 3A is an end view of a conceptualized example of a cylindrical isotropic porous scaffold 40A. Like the isotropic porous scaffold 2 of FIG. 1A, the isotropic porous scaffold 40A includes ligaments 42A defining cells or openings 44A. FIG. 3A conceptually depicts the ligaments 42A as being substantially straight and forming substantially uniform square-shaped openings 44A to better illustrate the effect of the deformation on the internal structure of the porous scaffold 40A as it is deformed. While uniform openings 44A defined by straight ligaments 42A are shown as making up the isotropic porous scaffold 40A, non-uniform shaped openings or cells and non-straight ligaments can make up the isotropic porous scaffold 40A.

FIG. 3B is an end view of an anisotropic porous scaffold 40B formed by deforming the isotropic porous scaffold 40A of FIG. 3A, such as by heating the porous scaffold 40A to or beyond a deformation temperature and compressing the scaffold inward along a vertical axis 46 while at or above the deformation temperature. The substantially circular-shaped isotropic porous scaffold 40A has been compressed into an oval-shaped anisotropic porous scaffold 40B. The anisotropic porous scaffold 40B includes ligaments 42B that are the deformed ligaments 42A of isotropic porous scaffold 40A. The ligaments 42B define cells or openings 44B in the porous scaffold 40A. Deforming the ligaments 42A of the isotropic porous scaffold 40A to form the ligaments 42B of anisotropic porous scaffold 40B results in openings 44B that are deformed versions of the openings 44A of the isotropic porous scaffold 40A.

In FIGS. 3A and 3B, the square-shaped openings 44A of the isotropic porous scaffold 40A are compressed in the direction of the vertical axis 46 to form rectangular openings 44B of the anisotropic porous scaffold 40B. For example, each opening 44A of the isotropic porous scaffold 40A can have a length L1A and a width W1A, while each opening 44B of the anisotropic porous scaffold 40B can have a length L1B and a width W1B. The widths W1A, W1B are measured generally parallel to the vertical axis 46 and the lengths L1A and L1B are measured generally parallel to a horizontal axis 48 that is generally perpendicular to the vertical axis 46. Compressing the isotropic porous scaffold 40A in the direction of the vertical axis 46 causes the width W1B of the anisotropic porous scaffold openings 44B to be smaller than the width W1A of the isotropic porous scaffold openings 44A. A scaffold such as scaffold 40A, or an area or segment of a scaffold, can be compressed to any suitable degree, and in this regard, it will be understood that the width of an opening such as opening 44A can be reduced any suitable amount, for example, to the depicted width W1B which is just one illustrative example of an amount or degree to which a width of this sort can be reduced. A reduced width such as width W1B, relative to a prior width such as width W1A, can amount to a percentage reduction in width falling anywhere in the range from about a 1% reduction in width to about a 90% reduction in width. In one example, such a width reduction is in the range from about 1% to about 10%. In another example, such a width reduction is in the range from about 5% to about 25%. In another example, such a width reduction is in the range from about 10% to about 30%. In another example, such a width reduction is in the range from about 15% to about 60%. In another example, such a width reduction is in the range from about 30% to about 70%. The length L1B of the anisotropic porous scaffold openings 44B remains substantially the same as the length L1A of the isotropic porous scaffold openings 44A. The resulting anisotropic porous scaffold 40B is stiffer in the direction of the horizontal axis 48 than in the direction of the vertical axis 46.

FIG. 4A is a top view of a conceptualized example of an oval-shaped cylindrical isotropic porous scaffold 50A. The isotropic porous scaffold 50A includes ligaments 52A defining cells or openings 54A. FIG. 4A conceptually depicts the ligaments 52A as being substantially straight and forming substantially uniform square-shaped openings 54A to better illustrate the deforming on the internal structure of the porous scaffold 50A as it is deformed. While uniform openings 54A defined by straight ligaments 52A are shown as making up the isotropic porous scaffold 50A, non-uniform shaped openings or pores and non-straight ligaments can make up the isotropic porous scaffold 50A.

FIG. 4B is an end view of an anisotropic porous scaffold 50B formed by deforming the isotropic porous scaffold 50A of FIG. 4A, such as by heating the porous scaffold 50A to or beyond a deformation temperature and stretching the scaffold outward along a vertical axis 56 while at or above the deformation temperature. The oval-shaped isotropic porous scaffold 50A has been stretched into a substantially circular anisotropic porous scaffold 50B. The anisotropic porous scaffold 50B includes ligaments 52B that are the deformed ligaments 52A of isotropic porous scaffold 50A. The ligaments 52B define cells or openings 54B in the porous scaffold 50B. Deforming the ligaments 52A of the isotropic porous scaffold 50A to form the ligaments 52B of anisotropic porous scaffold 50B results in openings 54B that are deformed versions of the openings 54A of the isotropic porous scaffold 50A.

In FIGS. 4A and 4B, the square-shaped openings 54A of the isotropic porous scaffold 50A are expanded in the direction of the vertical axis 56 to form rectangular openings 54B of the anisotropic porous scaffold 50B. For example, each opening 54A of the isotropic porous scaffold 50A can have a length L2A and a width W2A, while each opening 54B of the anisotropic porous scaffold 50B can have a length L2B and a width W2B, where the widths W2A, W2B are measured generally parallel to the vertical axis 56 and the lengths L2A and L2B are measured generally parallel to a horizontal axis 58 that is generally perpendicular to the vertical axis 56. The stretching of the isotropic porous scaffold 50A in the direction of the vertical axis 56 causes the width W2B of the anisotropic porous scaffold openings 54B to be larger than the width W2A of the isotropic porous scaffold openings 54A, while the length L2B of the anisotropic porous scaffold openings 54B remains substantially the same as the length L2A of the isotropic porous scaffold openings 54A. A scaffold such as scaffold 50A, or an area or segment of a scaffold, can be stretched to any suitable degree, and in this regard, it will be understood that the width of an opening such as opening 54A can be increased any suitable amount, for example, to the depicted width W2B which is just one illustrative example of an amount or degree to which a width of this sort can be increased. An increased width such as width W2B, relative to a prior width such as width W2A, can amount to a percentage increase in width falling anywhere in the range from about a 1% increase in width to about a 500% increase in width. In one example, such a width increase is in the range from about 5% to about 20%. In another example, such a width increase is in the range from about 10% to about 40%. In another example, such a width increase is in the range from about 25% to about 80%. In another example, such a width increase is in the range from about 40% to about 150%. In another example, such a width increase is in the range from about 60% to about 250%. The resulting anisotropic porous scaffold 50B has a greater stiffness in the direction of the vertical axis 56 relative to a stiffness in the direction of the horizontal axis 58.

FIG. 5A is a side cross-sectional view of a conceptualized example of a cylindrical isotropic porous scaffold 60A. The isotropic porous scaffold 60A includes ligaments 62A defining cells or openings 64A. FIG. 5A conceptually depicts the ligaments 62A as being substantially straight and forming substantially uniform square-shaped openings 64A to better illustrate the effect of the deforming on the internal structure of the porous scaffold 60A as it is deformed. It is to be understood that while uniform openings 64A defined by straight ligaments 62A are shown as making up the isotropic porous scaffold 60A, non-uniform shaped openings or pores and non-straight ligaments can make up the isotropic porous scaffold 60A.

FIG. 5B is a side cross-sectional view of an anisotropic porous scaffold 60B formed by deforming the isotropic porous scaffold 60A of FIG. 5A, such as by heating the porous scaffold 60A to or beyond a deformation temperature and deforming the scaffold while at or above the deformation temperature. The anisotropic porous scaffold 60B includes ligaments 62B that are the deformed ligaments 62A of isotropic porous scaffold 60A. The ligaments 62B define cells or openings 64B. Deforming the ligaments 62A of the isotropic porous scaffold 60A to form the ligaments 62B of anisotropic porous scaffold 60B results in openings 64B that are deformed versions of the openings 64A of the isotropic porous scaffold 60A.

In FIG. 5B, the anisotropic porous scaffold 60B can be formed by first deforming a first portion of the isotropic porous scaffold 60A and then secondly deforming a second portion of the isotropic porous scaffold 60B. The second deformation can be different than the first deformation, such as in magnitude, or direction, or both. Thus, the deformation of the isotropic porous scaffold 60A can be non-uniform. In FIG. 5B, the anisotropic porous scaffold 60B can be formed by first deforming at a first position 66 (e.g., compressing the isotropic porous scaffold 60A laterally inwardly by a first amount at the first position 66), by secondly deforming at a second position 68 (e.g., compressing the isotropic porous scaffold 60A laterally inwardly by a second amount at the second position 68), and by thirdly deforming at a third position 70 (e.g., stretching the isotropic porous scaffold 60A laterally outwardly at the third position 70).

In FIGS. 5A and 5B, the square-shaped openings 64A of the isotropic porous scaffold 60A can be compressed a first amount at the first position 66, can be compressed a second amount at the second position 68, and can be expanded at the third position 70. Openings 64B between these positions 66, 68, 70 can be compressed or expanded, depending on their location. The non-uniform compression or expansion of the openings 64A can result in generally trapezoidal-shaped openings 64B. For example, each opening 54A of the isotropic porous scaffold 50A can have a length L3A and a width W3A. Each opening 54B of the anisotropic porous scaffold 50B can have a length L3B and a width. The width of any particular opening 64B can depend on its location within the porous scaffold 60B. For example, the compression at the first location 66 can cause openings 64B at the first location 66 to have a width W3B1 that is smaller than the width W3A of the isotropic porous scaffold openings 64A. The compression at the second location 68 can cause openings 64B at the second location 68 to have a width W3B2 to be smaller than the width W3A of the isotropic porous scaffold openings 64A and smaller than the width W3B1 of the anisotropic porous scaffold openings 64B at the first location 66. The stretching of the isotropic porous scaffold 60A at the third location 70 can cause the width W3B3 of the anisotropic porous scaffold openings 64B at the third location to be larger than the width W3A of the isotropic porous scaffold openings 64A. The compression or expanding to form the anisotropic porous scaffold 60B can be only exerted in the direction of the widths, so the length L3B of the anisotropic porous scaffold openings 64B remains substantially the same as the length L3A of the isotropic porous scaffold openings 64A.

The anisotropic porous scaffold 60B can be further shaped, such as by machining or cutting, to provide a final desired shape that retains the non-uniform anisotropy of the anisotropic porous scaffold 60B. FIG. 5C shows an example of a resulting shaped anisotropic porous scaffold 60C formed by shaping the anisotropic porous scaffold 60B of FIG. 5B, such as by cutting or machining off one or more portions of the anisotropic porous scaffold 60B to form an outer edge 72 of the final shaped anisotropic porous scaffold 60C. In FIG. 5C, the shaped anisotropic porous scaffold 60C can be formed from the same ligaments 62B and openings 64B as the unshaped anisotropic porous scaffold 60B of FIG. 5B, but with a portion of some of the ligaments 62B removed.

Figure 6:
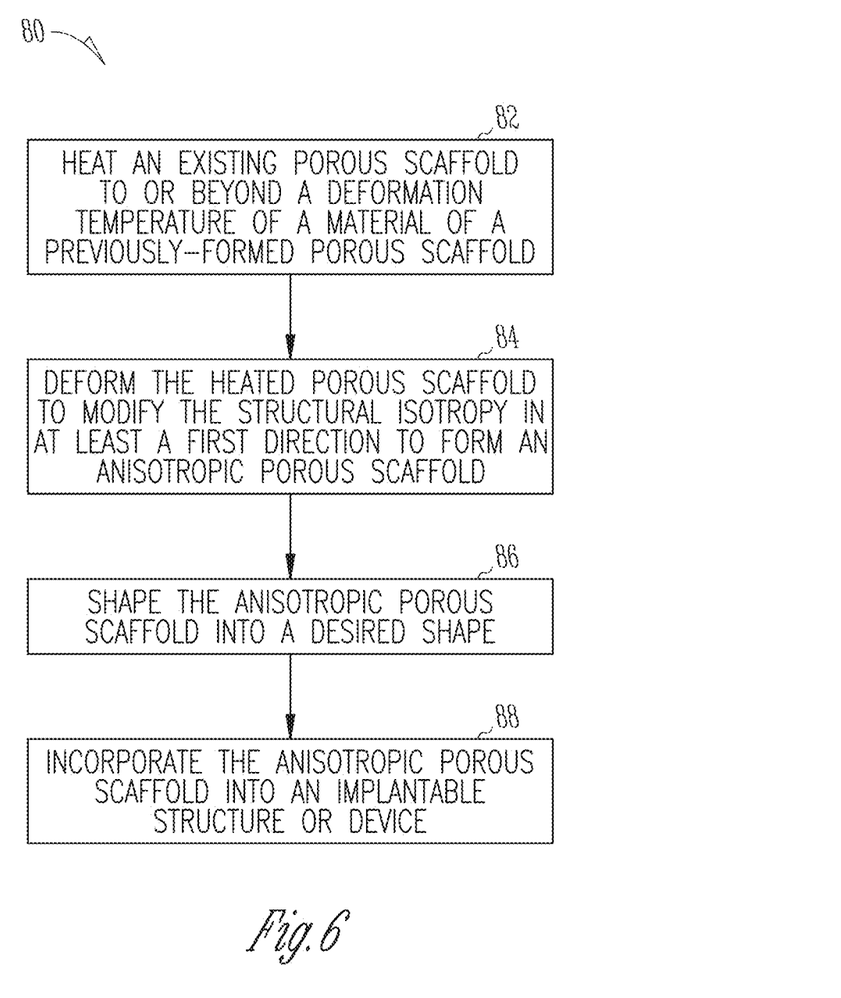
FIG. 6 is a diagram of an example of a method of manufacturing an anisotropic porous scaffold.

FIG. 6 is a flow diagram of an example of a method 80 for fabricating an anisotropic porous scaffold, such as the example of the porous scaffold 10 in FIG. 1B. At 82, a previously formed isotropic porous scaffold 2 can be heated to or beyond a deformation temperature of a material of the porous scaffold 2, such as at least to 60% of the absolute melting temperature of the material. At 84, the heated porous metal scaffold 2 can be deformed to modify the structural isotropy of the porous scaffold in at least a first direction, such as shown in FIG. 1B. The deforming can change the geometry of at least some of the pores, such as to establish the overall structural anisotropy of the porous scaffold 10 relative to the structural isotropy of the original porous scaffold 2. This can include collapsing pores in a first direction by compressing in that direction, or expanding pores in a second direction by stretching in the second direction, or both.

At 84, deforming can include first deforming a first portion of the porous scaffold, then secondly deforming a second portion of the porous scaffold. The second deformation can be different than the first deformation, such as in magnitude, direction, or both. For example, FIGS. 5A and 5B, show a first portion 66 of a cylindrical porous scaffold 60B that can be compressed by a first amount, a second portion 68 of the cylindrical porous scaffold 60B that can be compressed by a second, greater amount, and a third portion 70 of the cylindrical porous scaffold 60B that can be stretched rather than compressed.

Deforming the porous scaffold, at 84, can include active deforming, such as by using a tool or otherwise applying a force or pressure or vacuum to actively compress or stretch the porous scaffold, or can include passive deforming, such as by allowing the force of gravity to deform the porous scaffold while the porous metal scaffold is heated.

Figure 7:
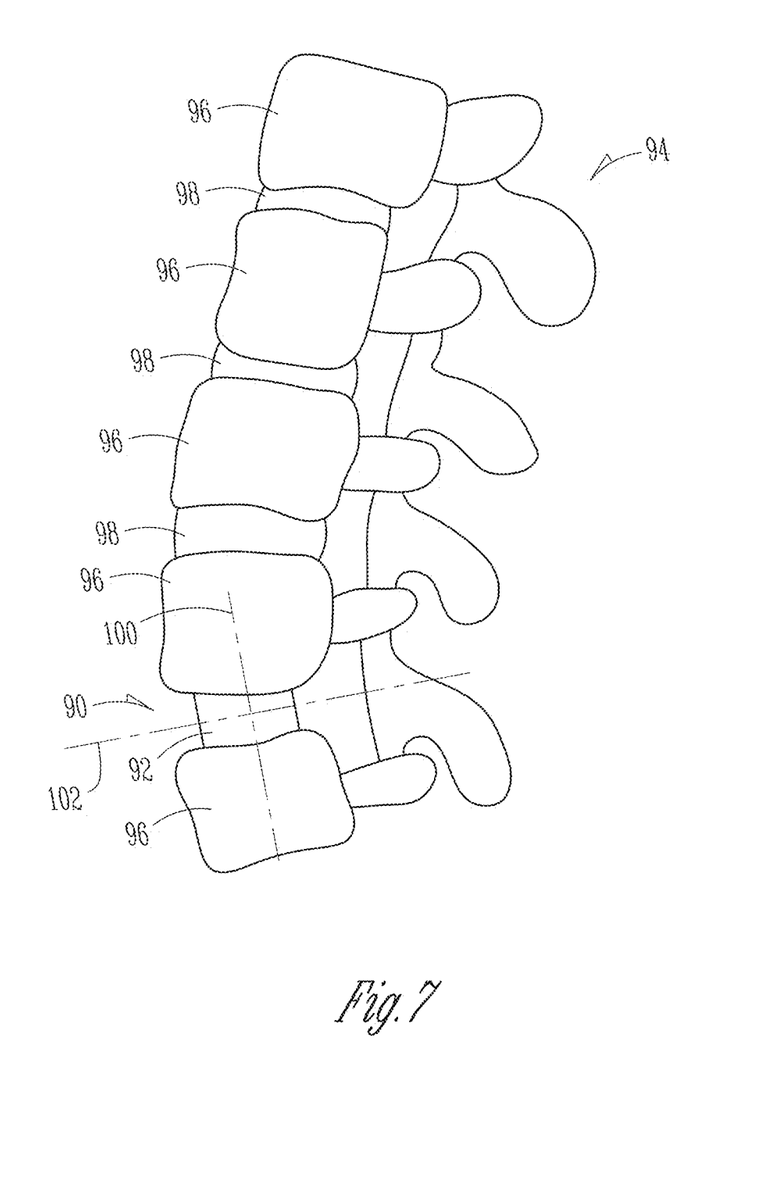
FIG. 7 is a schematic diagram of an example of a spine implant comprising an example of an anisotropic porous scaffold implanted in a patient's spine.
Figure 8:
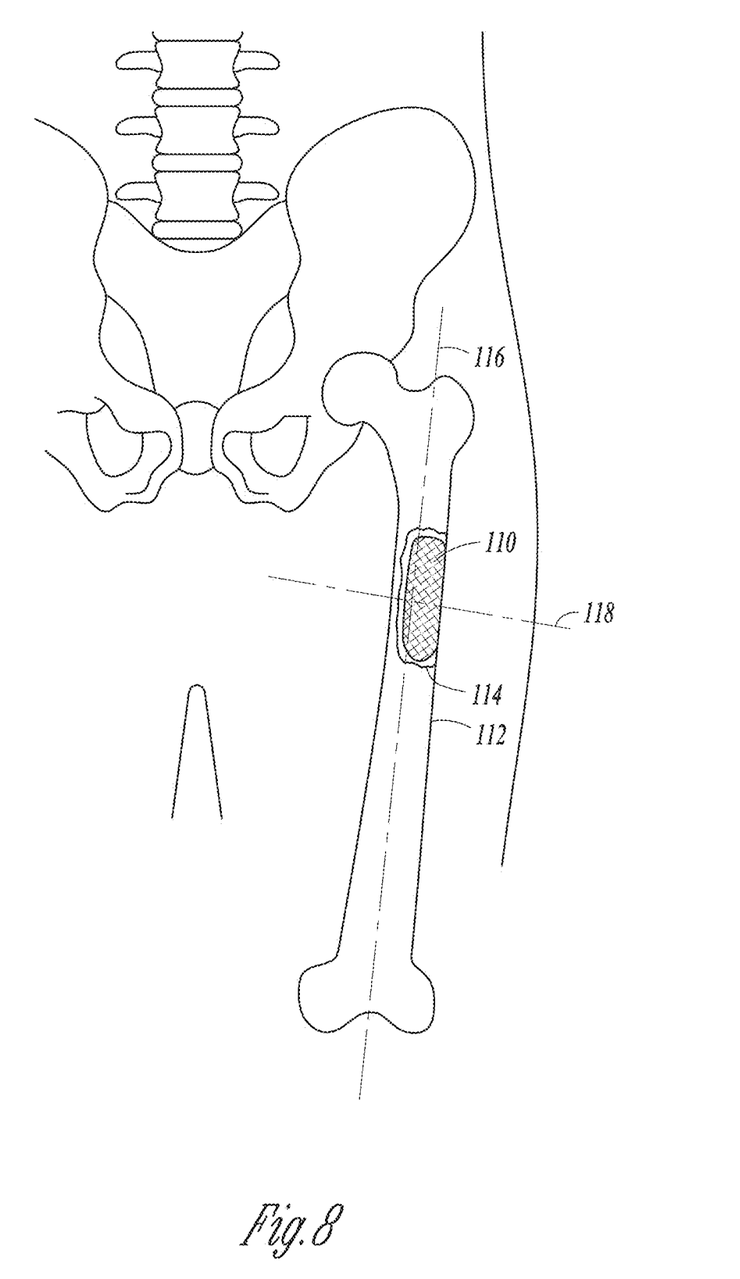
FIG. 8 is a schematic diagram of an example of a bone void filler comprising an example of an anisotropic porous scaffold implanted in a patient's femur.

At 86, the anisotropic porous scaffold 10 can be shaped as desired, such as in the shape of a support structure to be implanted into a patient, such as a spinal implant (see, e.g., FIG. 7) or a femoral support implant (see, e.g., FIG. 8). In FIGS. 5B and 5C, a formed anisotropic porous scaffold 60B can be further shaped, such as to change the macroscopic shape of a resulting shaped anisotropic porous scaffold 60C without changing the microscopic structure of the ligaments 62B and openings 64B that dictate the anisotropy of at least one physical property. Shaping of the anisotropic porous scaffold 10 include machining, cutting, grinding, trimming, or any other shaping technique.

At 88, the anisotropic porous scaffold 10 can be incorporated into an implantable structure or device, such as an implantable orthopedic device, for example, as a tibial cone of a tibial component of an orthopedic knee implant. Other implant examples can include, but are not limited to, a prosthetic shoulder implant, a prosthetic arm implant, a prosthetic elbow implant, a prosthetic finger implant, a prosthetic spine implant, a prosthetic toe implant, a prosthetic ankle implant, or a prosthetic trauma implant.

The method of forming an anisotropic porous scaffold, such as the porous scaffold 10, can allow for control of the orientation, the magnitude, or the location of one or more physical structural properties, such as stiffness, tensile strength, compressive strength, yield strength, fatigue strength, impact strength, density, or elastic modulus. The method can allow for a structure that is anisotropic with respect to one or more of the physical structural properties. The ability to control the orientation, the intensity, or the location of one or more physical structural properties, or to control the anisotropy of a porous scaffold, can allow for tailoring of the resulting porous structure. For example, the porous implant can be made stiffer in a first direction than in a second direction to control the amount of stress that is loaded onto the porous scaffold rather than adjacent bone or other tissue of the patient. Thus, the present method can allow control of the interaction between the porous scaffold and the adjacent tissue, allowing stress to be loaded onto the porous scaffold in some situations, onto the adjacent tissue in other situations, or onto both the porous scaffold and the adjacent tissue, in other situations.

In an orthopedic implant, such as a porous scaffold for structural support of a bone, the present method can control stress shielding by the porous scaffold. For example, the porous scaffold can be configured so that when an injured bone is first healing, the porous scaffold can have a stiffness that will carry stresses imposed on the bone, but once the bone repair has reached a certain point and the new bone has a desired stiffness or strength, the stiffness of the porous scaffold can be low enough relative to the bone stiffness so as to not overly shield the bone tissue from stress, since such stress shielding can lead to the inhibition of mineralization and maturation of new bone or can lead to the resorption of existing bone. The porous scaffold can be configured so that the value of a physical property is different in at least one direction with respect to the value of the physical property in a second direction, such as to substantially match a physical property of the porous scaffold to a corresponding physical property of the native bone.

FIG. 7 shows an example of a spine implant 90. The spine implant 90 can include an interbody cage 92 that can be implanted in the patient's spine 94, such as between a pair of vertebrae 96, such as within the lumbar region of the spine 94. The interbody cage 92 can be implanted in place of an intervertebral disc 98 that is normally positioned between adjacent vertebrae 96. The interbody cage 92 can help facilitate fusion between the pair of vertebrae 96 between which the interbody cage 92 is placed. The interbody cage 92 can be made in whole or in part from or using an anisotropic porous scaffold. The anisotropic porous scaffold can be made by a method such as described herein, for example, such that the strength or the stiffness of the interbody cage 92 can be increased in an axial direction 100 along the spine 94, relative to before the method was implemented. The anisotropic porous scaffold of the interbody cage 92 can be configured, such as using a method described herein, to be more flexible or less stiff in a lateral direction 102 compared to the flexibility or stiffness in the axial direction 100.

The stiffness in the axial direction 100 can be increased by starting with a previously-formed porous scaffold, such as an isotropic porous scaffold 2, which has a cross-sectional area in the lateral direction 102 that is larger than the final cross-sectional area of the interbody cage 92. Then, the previously-formed porous scaffold can be deformed, such as according to the present method, to compress the previously-formed porous scaffold down to the smaller cross-sectional size of the interbody cage 92, similar to the compression of the porous scaffold 40A to form the anisotropic porous scaffold 40B, as depicted in FIGS. 3A and 3B. Compressing the cross-sectional area will increase the density of ligaments within the porous scaffold of the interbody cage 92 that are oriented generally in the axial direction 100 and will, therefore, increase the stiffness in the axial direction 100.

FIG. 8 shows an example of bone void filler 110 implanted within a long bone, such as the femur 112 of a patient. The bone void filler 110 can be used to provide structural support to the femur 112 or other long bone after a large bone defect 114, such as a void or critical size defect, has formed in the femur 112 or other long bone. A "critical size" defect has a large enough void volume to be incapable of endogenous or spontaneous repair through normal osteogenesis. For example, in the human femur, a defect larger than about 2 centimeters can be considered a critical size defect. Such a defect can be the result of a trauma or accident, disease (such as from a cancerous mass), surgical manipulation, or prosthetic failure. The bone void filler 110 can be shaped and placed into the bone defect 114 with or without a bone graft material.

The bone void filler 110 can be made in whole or in part from an anisotropic porous scaffold, such as made by the present method. This can provide support for the femur 112, such as by configuring the bone void filler 110 to be stiffer in an axial direction 116 along the femur 112 than in a lateral direction 118.

Axial stiffness can be increased by starting with a previously-formed porous scaffold, such as an isotropic porous scaffold 2, that has a cross-sectional area in the lateral direction 118 that is larger than the final cross-sectional area of the bone void filler 110, followed by deforming the previously-formed porous scaffold using the present method to compress the previously-formed porous scaffold down to the smaller cross-sectional size of the bone void filler 110. This can be similar to the compression of the porous scaffold 40A to form the anisotropic porous scaffold 40B, as depicted in FIGS. 3A and 3B. Compressing the cross-sectional area will increase the density of ligaments within the porous scaffold of the bone void filler 110 that are oriented generally in the axial direction 116 and will, therefore, increase the stiffness in the axial direction 116.

In certain embodiments, a single previously-formed porous scaffold incorporates at least a first isotropic portion or region and a second, different isotropic portion or region where one or both of these portions or regions are then selectively deformed according to the techniques and methods described herein (e.g., stretched) to achieve a desired anisotropy within that portion or region. Such a previously-formed porous scaffold can incorporate any suitable number of such isotropic portions or regions, and the isotropic portions or regions can be arranged in any suitable fashion relative to one another. As well, any such isotropic portion or region can exhibit any suitable three-dimensional shape within the single, overall scaffold including being in layer and/or non-layer forms. Illustratively, such a previously-formed scaffold can include a first isotropic layer and a second isotropic layer where these layers may or may not be adjacent one another within the scaffold. Alternatively, such a previously-formed scaffold can include a first non-layer isotropic portion and a second non-layer isotropic portion where these portions may or may not be adjacent one another within the scaffold. Alternatively, such a previously-formed scaffold can include a first isotropic portion that is in non-layer form (e.g., a base component) and a second isotropic portion that is in layer form, for example, where the isotropic layer covers all or part of the base component, optionally with one or more intervening layers or portions. Where a previously-formed porous scaffold incorporates at least a first isotropic portion or region and a second, different isotropic portion or region, the difference between such first and second portions or regions can be any one or all of pore size, porosity, and density.

Figure 9:
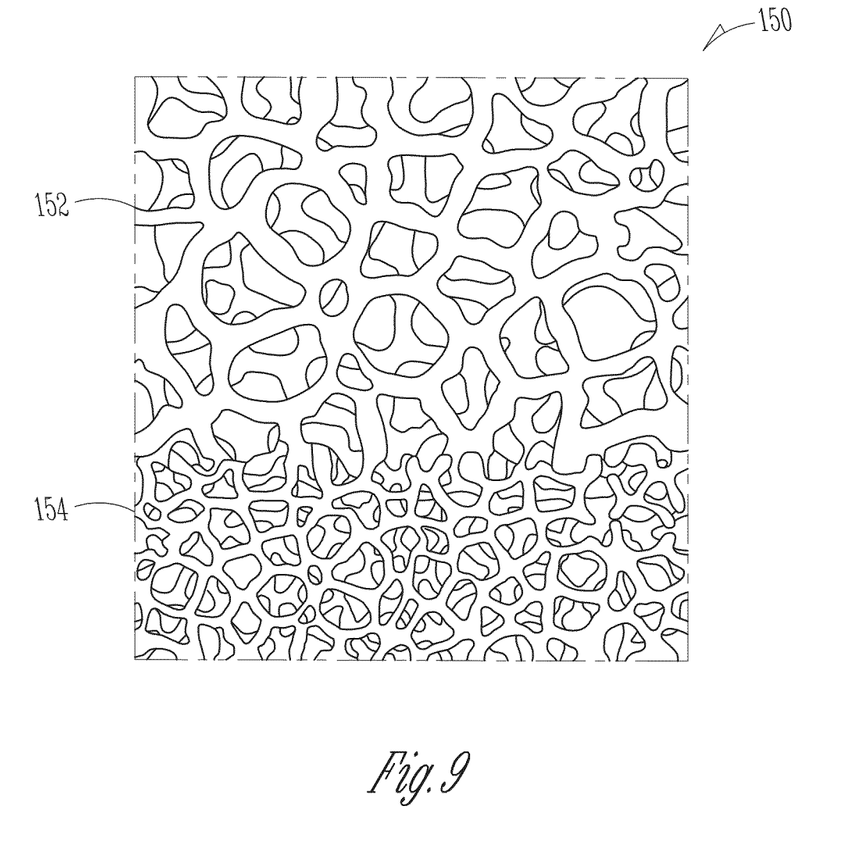
FIG. 9 is a side view of a porous scaffold.

With reference now to FIG. 9, shown is a previously-formed porous scaffold 150 that incorporates a first isotropic porous portion 152 and a second isotropic porous portion 154. One or both of these portions can be part of a layer or non-layer component of an orthopedic implant, and one or both of these portions can be part of an interior and/or exterior region (e.g., an exposed exterior surface) of an orthopedic implant, or a component thereof. As illustrated, the first isotropic porous portion 152 and the second isotropic porous portion 154 individually are both similar to the scaffold material shown in FIG. 1a except that the nominal pore size of scaffold 150 is relatively greater in first porous portion 152 as compared to second porous portion 154. While the transition from the first portion 152 to the second portion 154 can be generally abrupt as illustrated in FIG. 9, in some embodiments, the change in pore size and porosity may be more gradual so as to include a sort of transition portion or region between first portion 152 and second portion 154.

In some embodiments, a porous scaffold such as that illustrated in FIG. 9 may comprise a reticulated vitreous carbon (RVC) substrate which itself has a generally uniform pore size but where a greater amount of a biocompatible metal, such as tantalum, is infiltrated and coated on the ligaments of the carbon substrate in the second portion 154 than in the first portion 152, resulting in the second portion having decreased pore size. This may be accomplished by masking a portion of the carbon substrate during the infiltration and deposition process, or, following an initial extent of infiltration and deposition of the metal, by at least partially filling a sacrificial material into the pores of one of the layers, followed by carrying out further infiltration and deposition of the metal into the pores of the other layer and then removing the sacrificial material. Similar methods and techniques are disclosed in co-pending U.S. application Ser. No. 61/703,946, filed Sep. 21, 2012, titled "VARIABLE DENISTY IMPLANT AND METHOD" which is hereby incorporated by reference herein in its entirety. In some embodiments, an underlying RVC substrate itself is manufactured to include at least two identifiable isotropic regions having relatively different porosities, and the various ligaments of the carbon substrate within those regions are generally uniformly coated with a biocompatible metal such as tantalum (e.g., resulting in a substantially uniform coating thickness on all ligaments) so as to generate a porous metal scaffold such as that shown in FIG. 9 where a second portion such as second portion 154 has a decreased pore size relative to a different portion or region even though the metal coating thickness in the different regions is essentially the same.

To better illustrate the method and porous scaffold disclosed herein, a non-limiting list of examples is provided here:

Example 1 can include subject matter (such as an apparatus, a device, a method, or one or more means for performing acts), such as can include a method of fabricating an anisotropic porous scaffold. The subject matter can comprise heating a previously-formed porous metal scaffold to permit deformation of a material of the previously-formed porous metal scaffold, and deforming, when heated, the previously-formed porous metal scaffold in at least a first direction.

Example 2 can include, or can optionally be combined with the subject matter of Example 1, to optionally include the porous metal scaffold being structurally anisotropic after deforming the previously-formed porous metal scaffold.

Example 3 can include, or can optionally be combined with the subject matter of one or any combination of Examples 1 or 2, to optionally include the heating the previously-formed initial porous metal scaffold comprising heating the previously-formed initial porous metal scaffold to at least 60% of an absolute melting temperature of the material of the previously-formed porous metal scaffold.

Example 4 can include, or can optionally be combined with the subject matter of one or any combination of Examples 1-3, to optionally include the previously-formed porous metal scaffold comprising a plurality of cells defined by ligaments, wherein deforming the heated initial porous metal scaffold comprises collapsing at least some of the cells in the first direction.

Example 5 can include, or can optionally be combined with the subject matter of one or any combination of Examples 1-4, to optionally include the initial porous metal scaffold being structurally isotropic before the heating of the initial porous metal scaffold.

Example 6 can include, or can optionally be combined with the subject matter of one or any combination of Examples 1-5, to optionally include the deforming of the heated initial porous metal scaffold comprising compressing the heated initial porous metal scaffold in the first direction.

Example 7 can include, or can optionally be combined with the subject matter of one or any combination of Examples 1-6, to optionally include the porous scaffold having a porosity of at least about 60% after deforming the heated previously-formed porous scaffold.

Example 8 can include, or can optionally be combined with the subject matter of one or any combination of Examples 1-7, to optionally include the structurally anisotropic porous scaffold comprising a plurality of cells interconnected by pores, wherein at least about 80% of the plurality of cells are interconnected after deforming the heated previously-formed porous scaffold.

Example 9 can include, or can optionally be combined with the subject matter of one or any combination of Examples 1-8, to optionally include the deforming of the heated previously-formed porous scaffold comprising providing a deformed porous scaffold having a physical property with a value in a second direction that is different from a value of the physical property in a third direction that is different than the second direction.

Example 10 can include, or can optionally be combined with the subject matter of one or any combination of Examples 1-9, to optionally include the second direction being substantially parallel to the first direction.

Example 11 can include, or can optionally be combined with the subject matter of one or any combination of Examples 1-9, to optionally include the second direction is substantially perpendicular to the first direction.

Example 12 can include, or can optionally be combined with the subject matter of one or any combination of Examples 1-11, to optionally include the third direction being substantially perpendicular to the second direction.

Example 13 can include, or can optionally be combined with the subject matter of one or any combination of Examples 1-12, to optionally include the deforming the heated previously-formed porous scaffold comprising providing a deformed porous scaffold with a value of a physical property in a second direction that is substantially the same as a corresponding physical property of a tissue in the second direction and providing the deformed porous scaffold with a value of the physical property in a third direction is substantially the same as the corresponding physical property of the tissue in the third direction.

Example 14 can include, or can optionally be combined with the subject matter of one or any combination of Examples 1-13, to optionally include the deforming the heated previously-formed porous scaffold comprising forming a first deformation at a first location of the heated previously-formed porous scaffold and forming a second deformation at a second location of the heated previously-formed porous scaffold, wherein the second deformation is different from the first deformation.

Example 15 can include, or can optionally be combined with the subject matter of one or any combination of Examples 1-14, to optionally include shaping the structurally anisotropic porous scaffold.

Example 16 can include, or can optionally be combined with the subject matter of one or any combination of Examples 1-3, to optionally include incorporating the structurally anisotropic porous scaffold into an implantable structure or device comprising at least one of a prosthetic shoulder implant, a prosthetic arm implant, a prosthetic elbow implant, a prosthetic finger implant, a prosthetic spine implant, a prosthetic toe implant, a prosthetic ankle implant, and a prosthetic trauma implant.

Example 17 can include, or can optionally be combined with the subject matter of one or any combination of Examples 1-16, to include subject matter (such as an apparatus, a device, a method, or one or more means for performing acts), such as can include a porous scaffold. The subject matter can include a plurality of cells defined by ligaments, a plurality of the cells being interconnected by pores. The plurality of ligaments can provide for a physical property of the porous scaffold, with a value of the physical property in a first direction being different from a value of the physical property in a second direction that is different than the first direction.

Example 18 can include, or can optionally be combined with the subject matter of one or any combination of Examples 1-17, to optionally include at least a first set of the plurality of cells each having a length in the first direction that is different from a length of each of the first set of cells in the second direction.

Example 19 can include, or can optionally be combined with the subject matter of one or any combination of Examples 1-18, to optionally include the value of the physical property in the first direction being substantially the same as a corresponding physical property of a tissue in the first direction and providing the value of the physical property in the second direction that is substantially the same as the corresponding physical property of the tissue in the second direction.

Example 20 can include, or can optionally be combined with the subject matter of one or any combination of Examples 1-19, to optionally include the second direction is substantially perpendicular to the first direction.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method of fabricating an anisotropic porous scaffold, the method comprising:
heating a previously-formed porous metal scaffold to permit deformation of a metal material of the previously-formed porous metal scaffold, wherein said heating comprises heating the previously-formed porous metal scaffold to between 40% and 80% of an absolute melting temperature of said metal material of the previously-formed porous metal scaffold; and
deforming, when heated, the previously-formed porous metal scaffold in at least a first direction.

2. The method of claim 1, wherein heating the previously-formed porous metal scaffold comprises heating the previously-formed porous metal scaffold to at least 60% of the absolute melting temperature of said metal material of the previously-formed porous metal scaffold.

3. The method of claim 1, wherein deforming the heated previously-formed porous metal scaffold comprises compressing the heated previously-formed porous metal scaffold in the first direction.

4. The method of claim 1, wherein the porous metal scaffold has a porosity of at least 60% after deforming the heated previously-formed porous scaffold.

5. The method of claim 1, wherein, deforming the heated previously-formed porous metal scaffold comprises providing a deformed porous scaffold with a value of a physical property in a second direction that is substantially the same as a corresponding physical property of a tissue in the second direction and providing the deformed porous metal scaffold with a value of the physical property in a third direction is substantially the same as the corresponding physical property of the tissue in the third direction.

6. The method of claim 1, wherein deforming the heated previously-formed porous metal scaffold comprises forming a first deformation at a first location of the heated previously-formed porous metal scaffold and forming a second deformation at a second location of the heated previously-formed porous metal scaffold, wherein the second deformation is different from the first deformation.

7. The method of claim 1, wherein the previously-formed porous metal scaffold is structurally isotropic before the heating of the previously-formed porous metal scaffold.

8. The method of claim 1, wherein deforming the heated previously-formed porous metal scaffold comprises providing a deformed porous metal scaffold having a physical property with a value in a second direction that is different from a value of the physical property in a third direction that is different than the second direction.

9. The method of claim 1, wherein the porous metal scaffold is structurally anisotropic after deforming the previously-formed porous metal scaffold.

10. The method of claim 1, wherein the previously-formed porous metal scaffold comprises a plurality of cells defined by ligaments, wherein deforming the heated previously-formed porous metal scaffold comprises collapsing at least some of the cells in the first direction.

11. The method of claim 9, wherein the structurally anisotropic porous scaffold comprises a plurality of cells interconnected by pores, wherein at least 80% of the plurality of cells are interconnected after deforming the heated previously-formed porous metal scaffold.

12. The method of claim 9, comprising shaping the structurally anisotropic porous scaffold.

13. The method of claim 9, comprising incorporating the structurally anisotropic porous scaffold into an implantable structure or device comprising at least one of a prosthetic shoulder implant, a prosthetic arm implant, a prosthetic elbow implant, a prosthetic finger implant, a prosthetic spine implant, a prosthetic toe implant, a prosthetic ankle implant, and a prosthetic trauma implant.

14. A method of fabricating an anisotropic porous scaffold, the method comprising:
heating a previously-formed porous metal scaffold to permit deformation of a metal material of the previously-formed porous metal scaffold, wherein the previously-formed porous metal scaffold comprises a plurality of cells defined by ligaments; and
deforming, when heated, the previously-formed porous metal scaffold in at least a first direction, wherein deforming the heated previously-formed porous metal scaffold comprises collapsing at least some of the cells in the first direction.

15. A method of fabricating an anisotropic porous scaffold, the method comprising:
heating a previously-formed porous metal scaffold to permit deformation of a metal material of the previously-formed porous metal scaffold, wherein the previously-formed porous metal scaffold is structurally isotropic before the heating of the previously-formed porous metal scaffold; and
deforming, when heated, the previously-formed porous metal scaffold in at least a first direction.

16. The method of claim 15, wherein deforming the heated previously-formed porous metal scaffold comprises providing a deformed porous metal scaffold having a physical property with a value in a second direction that is different from a value of the physical property in a third direction that is different than the second direction.

17. The method of claim 15, wherein the porous metal scaffold has a porosity of at least 60% after deforming the heated previously-formed porous scaffold.

18. A method of fabricating an anisotropic porous scaffold, the method comprising:
heating a previously-formed porous metal scaffold to permit deformation of a metal material of the previously-formed porous metal scaffold; and
deforming, when heated, the previously-formed porous metal scaffold in at least a first direction, wherein deforming the heated previously-formed porous metal scaffold comprises providing a deformed porous metal scaffold having a physical property with a value in a second direction that is different from a value of the physical property in a third direction that is different than the second direction.

19. The method of claim 18, wherein the second direction is substantially parallel to the first direction.

20. The method of claim 18, wherein the second direction is substantially perpendicular to the first direction.

21. The method of claim 18, wherein the third direction is substantially perpendicular to the second direction.

* * * * *